(12) United States Patent
Kodvanj et al.

(10) Patent No.: US 11,786,281 B2
(45) Date of Patent: Oct. 17, 2023

(54) SCREW WITH A VARIABLE LOCKING ANGLE AND A CORRESPONDING LOCKING SYSTEM

(71) Applicants: Janos Kodvanj, Zagreb (HR); Srecko Sabalic, Zagreb (HR)

(72) Inventors: Janos Kodvanj, Zagreb (HR); Srecko Sabalic, Zagreb (HR)

(73) Assignee: ORTHOLOCK D.O.O., Zagreb (HR)

( * ) Notice: Subject to any disclaimer, the term of this patent is extended or adjusted under 35 U.S.C. 154(b) by 323 days.

(21) Appl. No.: 17/376,176

(22) Filed: Jul. 15, 2021

(65) Prior Publication Data

US 2021/0338292 A1 Nov. 4, 2021

Related U.S. Application Data

(63) Continuation of application No. 17/159,146, filed on Jan. 27, 2021, now Pat. No. 11,083,507, which is a continuation of application No. PCT/EP2020/051202, filed on Jan. 18, 2020.

(30) Foreign Application Priority Data

Mar. 6, 2019 (HR) .............................. P20190451A (51) Int. Cl.
*A61B 17/80* (2006.01)
*A61B 17/86* (2006.01)

(52) U.S. Cl.
CPC ...... *A61B 17/8057* (2013.01); *A61B 17/8615* (2013.01); *A61B 17/8635* (2013.01)

(58) Field of Classification Search
CPC ...................... A61B 17/8605; A61B 17/8057
See application file for complete search history.

(56) References Cited

U.S. PATENT DOCUMENTS

| 5,275,601 A | 1/1994 | Gogolewski et al. |
| 10,561,450 B2 | 2/2020 | Thiel et al. |
| 2004/0073218 A1 | 4/2004 | Dahners |

(Continued)

FOREIGN PATENT DOCUMENTS

| DE | 10 2010 038949 A1 | 2/2012 |
| FR | 2890848 A1 | 3/2007 |

(Continued)

OTHER PUBLICATIONS

International Search Report and Written Opinion dated May 25, 2020, received for PCT Application PCT/EP2020/051202, Filed on Jan. 18, 2020, 13 pages.

(Continued)

*Primary Examiner* — David W Bates
(74) *Attorney, Agent, or Firm* — XSENSUS LLP (57) ABSTRACT

A locking system can comprise a screw head without threads and a thread created only inside a bore of a bone plate. The machining of thread geometry can thus pertain to the screw body, while the screw head can be formed by curved surfaces and contact surfaces by simple machining process. A plurality of screws can be implemented, and each bone plate can have a larger number of bores for accepting the screws than the number of screws. The said locking screw can be used with other bone plates having continuous or partial threads created inside their bores.

13 Claims, 7 Drawing Sheets

(56) References Cited

U.S. PATENT DOCUMENTS

| | | | |
|---|---|---|---|
| 2007/0043366 A1* | 2/2007 | Pfefferle | A61B 17/8061 606/279 |
| 2007/0083207 A1 | 4/2007 | Ziolo et al. | |
| 2008/0140130 A1 | 6/2008 | Chan et al. | |
| 2010/0312285 A1 | 12/2010 | White et al. | |
| 2014/0005728 A1 | 1/2014 | Koay et al. | |
| 2014/0018862 A1 | 1/2014 | Koay et al. | |
| 2015/0142063 A1 | 5/2015 | Austin et al. | |
| 2015/0190185 A1 | 7/2015 | Koay et al. | |
| 2015/0359575 A1 | 12/2015 | Pech et al. | |
| 2016/0331426 A1 | 11/2016 | Tao et al. | |
| 2017/0042595 A1 | 2/2017 | Terrill et al. | |
| 2017/0319248 A1 | 11/2017 | Milella, Jr. et al. | |
| 2018/0235681 A1* | 8/2018 | Chambers | A61B 17/8057 |

FOREIGN PATENT DOCUMENTS

| | | |
|---|---|---|
| FR | 3010892 A1 | 3/2015 |
| WO | 2015/020789 A1 | 2/2015 |

OTHER PUBLICATIONS

International Preliminary Report on Patentability dated Dec. 3, 2020, received for PCT Application PCT/EP2020/051202, Filed on Jan. 18, 2020, 20 pages.

\* cited by examiner

SCREW WITH A VARIABLE LOCKING ANGLE AND A CORRESPONDING LOCKING SYSTEM

CROSS-REFERENCE TO RELATED APPLICATIONS

This application is a continuation of U.S. application Ser. No. 17/159,146, filed Jan. 27, 2021, which is a continuation of International App. No. PCT/EP2020/051202 filed Jan. 18, 2020, which claims the benefit of priority to Croatian (HR) Patent App. No. P20190451A filed Mar. 6, 2019, wherein the entire contents and disclosure of each of the foregoing applications is incorporated by reference herein in its entirety.

FIELD

The present disclosure relates to a screw with a variable locking angle into the plate and a corresponding locking system. In a broader sense, embodiments of the present disclosure belong to the field of surgical instruments, aids and procedures specially designed for application on bones and joints, for example for osteosynthesis, where utilized plates and screws are specifically designed for such purposes. More specifically, the field can be described as a locking system in which the screw head is locked into a bore on the bone plate in such a way that the element that performs the locking itself is the thread machined in the bone plate.

TECHNICAL PROBLEM

A basic technical problem that is solved by select locking systems is that such a system delivers a simple and effective locking of the screw head inside the plate while simultaneously anchoring the screw body inside the bone. This is also the case with embodiments of the present disclosure, which can allow a variable locking angle, in the range of −20° to 20°, to be achieved measured in relation to the base, i.e., the axis of the bone plate bore in all allowable directions. The bone plates are made of titanium, titanium alloy with aluminum, and/or vanadium and/or niobium, or with any other suitable biocompatible material and each plate is equipped with at least two bores where screws are inserted into. The screws, to be used for variable locking of the screw head into plates, are also made of the same or very similar materials. However, the bone plates come with various geometries to be adaptable to any situation the surgeon may be confronted with and for very specific applications. Also, depending on the site and type of fracture—multiple dimensions of the same geometry suit for a diverse patient population. In the case of osteosynthesis plates, each such plate is equipped with multiple bores. So, an average plate contains 4-20 bores in which an average of 4-10 screws will be inserted during an operation. Usually some bores on the plate remain unused.

In addition to the formation of geometry which corresponds with the application of the plate to a particular bone, the plate machining process therefore includes also the process of cutting threads in multiple bores. As we will see in the background art elaboration, these threads are sometimes very specific. Therefore, every bore that is processed in a non-standard way; here under a non-standard way we understand a method that is different from the usual tapered threading or parallel threading—represents an additional cost of production. If a screw bore remains unused in the application, since only a certain number of specifically machined bores on the plate are actually used in surgical intervention, this significantly increases the price of the locking system. Such locking systems are well known in the art. They consist of a bone plate which is softer than the used material to form the screw with thread on its head. During the application, said screw head is carved into the specifically machined bores formed in the bone plates and then said screw is "locked" into the plate and a firm bond between the screw head and the said plate is formed.

A first technical problem addressed by embodiments of the present disclosure is the observed surplus of complexly manufactured but unused bores on the bone plate, as not all bores are necessary. Namely, the proposed new locking system shifts the machining process complexity exclusively to the newly designed screw, while the plate and its bores can be subjected to relatively simple standard bore formation equipped with ordinary tapered threading or parallel threading. In embodiments of the present disclosure, a screw head is made from a softer material than the used bone plate material. During the locking process, the plate causes damages to the specifically designed screw head and lock it within the said plate. It has been mentioned already that not all bores on the standard plate are used in practice, so the production of this system is significantly more economical, and consequently, the surgical procedure is more cost-effective. As will be seen, this first technical problem can be solved by implementing a novel and specific screw head geometry yielding the same locking or even better locking results than inverse systems with a plate made of a softer material and the screw head made of a harder material.

In addition to its use with a bone plate with standard threads, the newly designed screw can be used in systems with non-standard threads without any modification. The only requirement can be that the hardness of the non-standard threaded plate is higher than the hardness of the used screw, i.e., the screw head. The latter fact contributes to the possibility of combining parts of different locking kits in the cases or conditions such as natural disasters or wartime conditions, when the availability of plate sets and compatible screws may be limited.

The newly designed screw can be easy to manufacture due to the fact that it does not contain a thread on its head, only relatively simple machined surfaces. Such geometry is considerably simpler compared to similar screws in the art, without compromising the quality of its locking capabilities. Of course, the application of the newly designed system is not limited to its use in medicine only, but this system can also be applied in a variety of industries, where it is necessary to lock the screw into a structural element, and where this screw tightens the surface of one element to any regular or irregular geometry of another structural element and when a firm connection needs to be created between them.

THE BACKGROUND ART

Numerous technical solutions of specifically designed screw heads that are locked into bone plates have been disclosed in background art.

US patent application published as US2017/0319248A1 for the invention: "Variable-angle locking screws, and bone plate systems that include variable-angle locking screws", filed in the name of Cardinal Health 247 Inc., discloses a specifically designed screw that locks into the plate. The aforementioned screw is designed with specifically shaped segments on the screw head which is not circular but segmented. However, this screw head has additional threads that are carved into the plate, which is not the case with one or more embodiments of the present disclosure. A screw designed in the way presented according to one or more embodiments of the present disclosure can be used with plates with bores that have or do not have a thread. However, it is clear from this document that the material used for making such a screw is harder than the material of the plate itself and that the process of making such a screw is significantly more complex than the process of making the screw presented according to embodiments of the present disclosure.

US patent application published as US2010/0312285A1 for the invention: "Bone Plate Assembly", filed in the name of Greatbatch Ltd., discloses, inter alia, a screw that locks into a plate at a certain angle. The head of the screw is produced in segments that have a thread which is carved into the bone plate bores. Said bores are irregular in shape and are equipped with thread that accept the thread of the screw head. The complexity of making the plate with such bores is a technical characteristic that is avoided by a technical solution according to one or more embodiments of the present disclosure, without compromising the locking abilities.

US patent application published as US2017/0042595A1 for the invention: "Polyaxial Locking Mechanism", filed in the name of Rightholder Zimmer Inc., discloses a screw that locks with its head into the bone plate. As in the previous technical solution, the screw head is equipped with a thread which interlocks with the plate thread. As with the previous disclosure, the screw head is segmented, but also additionally fitted with a thread; this is not the case according to one or more embodiments of the present disclosure, as this otherwise can further complicate the production of such a screw head considerably as well as the corresponding bone plate.

A very similar solution to the previous one is found in the US patent application US2007/0083207A1 for the invention: "Variable angle bone fixation assembly", filed in the name of Ziolo Tara et al. This invention evidently requires complicated machining of the screw head and every bore in the corresponding plate.

Following the same concept of screws with special head geometries there is also another technical solution disclosed in the US patent application US2015/0190185A1 for the invention "Variable Angle Bone Fixation Device", filed in the name of Depuy Synthes Products Inc. This document discloses a specifically designed screw that allows its head to be locked into a plate that is equipped with very complex bores whose manufacturing is certainly very complex.

US patent application published as US2015/0142063A1 for the invention: "Systems and Methods for Using Polyaxial Plates", filed in the name of Smith & Nephew Inc., discloses a specifically designed screw head with wings that interact with the thread created in the plate bore. The screw head is of a rather complicated design.

FR patent application published as FR3010892A1 for the invention: "Ensemble comprenant une piece implantable destinee a etre fixee a un ou plusieurs os ou a des parties d'os a reunir, et au moins une vis de fixation de cette piece implantable a cet ou ces os" which translated reads "Set including an implantable part intended to be fixed to one or more bones or to parts of bones to be joined, and at least one fixation screw of this implantable part to this or these bones", filed in the name of Groupe Lepine.

Document FR3010892A1 discloses a screw with rounded head and with longitudinal wide grooves formed on it—but without thread on the said head. The cited screw construction has edges at the end of the said grooves that lock the screw head within the specifically designed bone plate hole for receiving said dedicated screw head. From the disclosed figures, it is evident that the screwing and locking of this screw head is performed by screwing for ⅓ of the circle, i.e., close to 120°, that is sufficient for normal screwing but perhaps with limited locking strength in case of polyaxial screwing of the said screw. Furthermore, this disclosure requires very specific plate holes that limits versatile use of the said fastener described in the disclosure.

FR patent application published as FR2890848A1 for the invention: "Dispositif d'osteosynthese" which translated reads "Osteosynthesis device", filed in the name of DLP Societe responsabilité limitée teaches about the screw formed as a rounded head without thread. The corresponding bone plate is thus formed with a plurality of segmented bone plate holes with carving means that cut into the said rounded head and lock the mentioned screw head. Complex and expensive bone plate holes with carving means limit the usage of the fastener described in the disclosure.

All previously mentioned technical solutions define general background art for the hereby disclosed invention. A technical solution published in the form of international PCT patent application WO2015/020789A1 for the invention: "Orthopedic Screw Fastener System including Screws", filed in the name of Flower Orthopedics Corp. Inc., discloses a locking system of screw and plate to which we herein refer.

Figure 1:
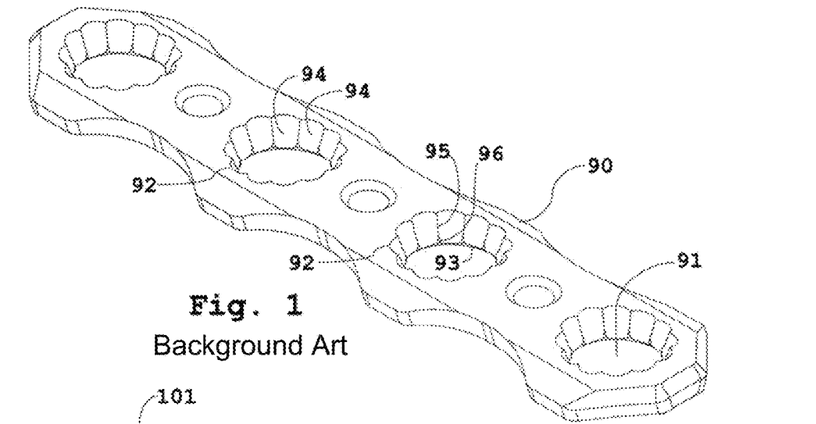
FIGS. 1 and 3 illustrate a bone plate constructed according to a background art solution.
Figure 2:
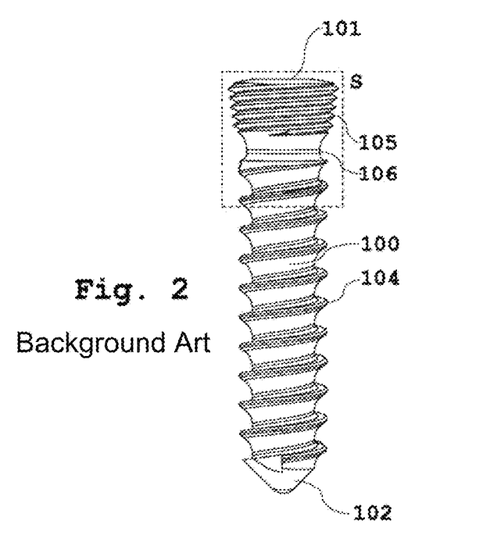
Figure 2A:
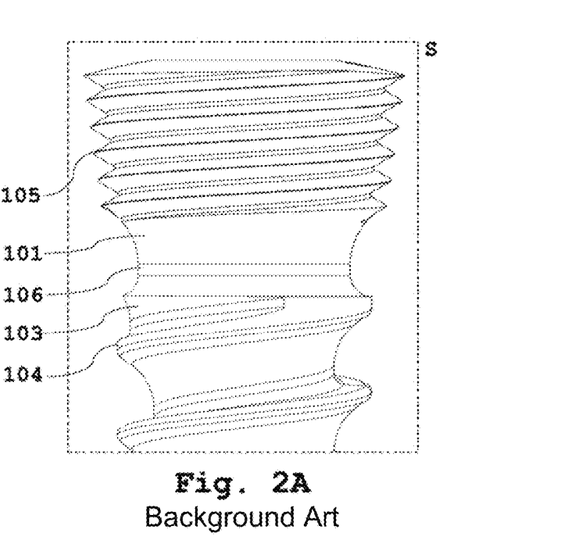
FIG. 2A illustrates the detail S of the screw head shown in FIG. 2, according to the aforementioned background art solution.
Figure 3:
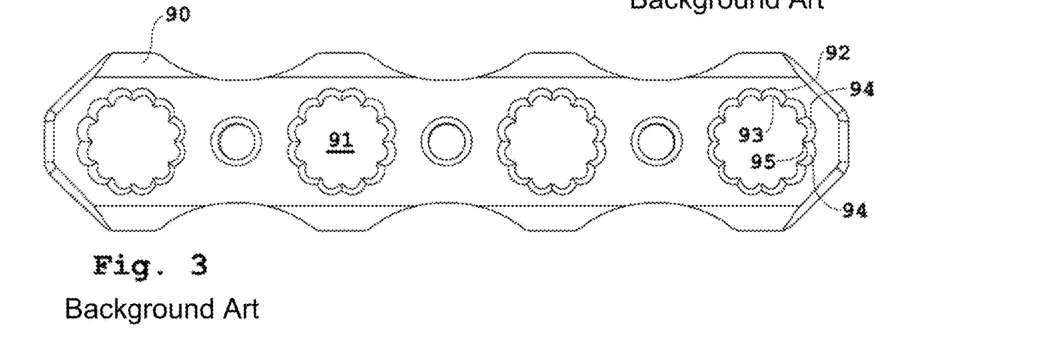
Figure 4A:
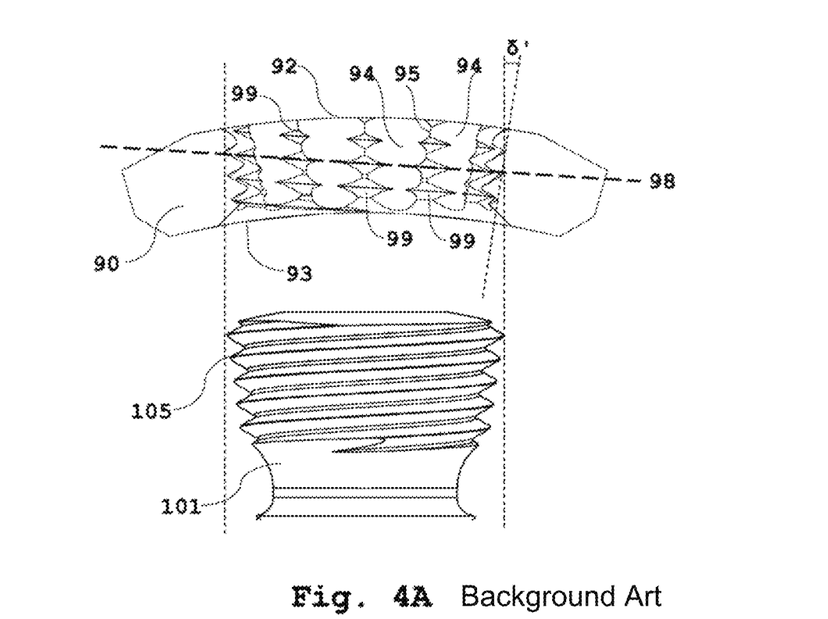
FIGS. 4A and 4B depict damage that can occur in the plate bores, shown in FIGS. 1 and 3, according to the aforementioned background art solution.

FIGS. 1, 2, 2A, 3, 4A and 4B herein correspond to this "Background art." FIGS. 1 and 3 depict a bone plate (90) with multiple bores (91) for receiving a screw head (101) with a thread (105). Each bore (91) is cone-shaped, with a cone slope δ' as indicated in FIG. 4A and extends from the upper edge (92) to the bottom edge (93) of the plate (90), where said bore (91) is machined in a way that forms curved sections (94). The sections are machined in a way that they are inclined at an angle δ' relative to the bore axis. Two neighboring curved sections are interconnected by the intersection line (95) which grows into a contact surface (96) near the bottom edge (93) of the bore (91). The plate is made of the material that is softer than the material of the screw (100) shown in FIG. 2. The screw (100), which locks its head into the bore (91) of the bone plate (90), consists of a screw head (101) with a thread (105), tip of the screw (102) made on the screw body (103) on which there is a self-cutting thread (104). The screw head (101) and the screw body (103) meet at the joint (106); see FIG. 2 and FIG. 2A, where FIG. 2A represents detail S from FIG. 2.

Figure 4B:
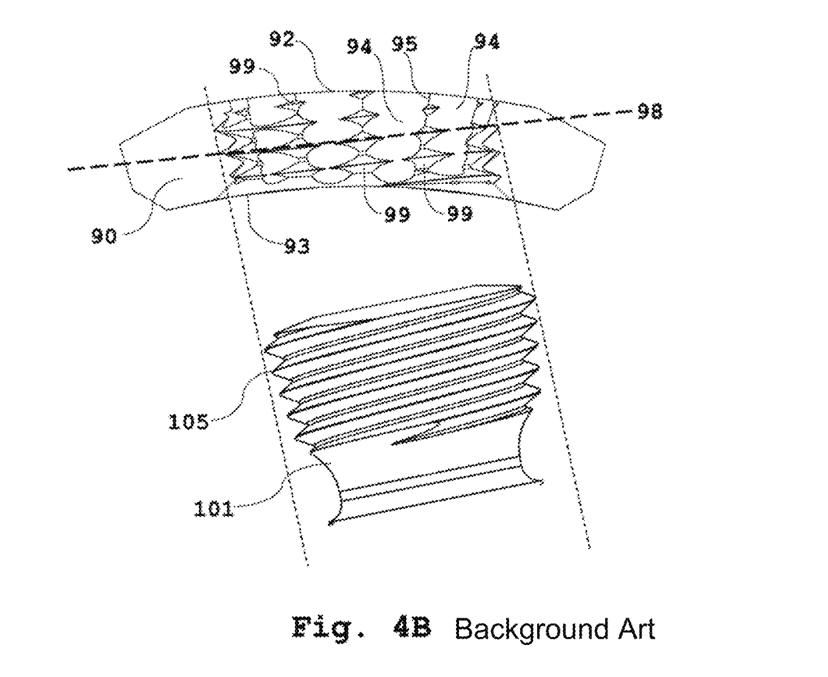

The way the locking system functions is shown in detail in FIGS. 4A and 4B. FIG. 4A illustrates the case when the screw is inserted at an angle of 0° relative to the bore (91) axis. A portion of the plate (90) is shown through the bore (91) cross-section, which is located behind the screw head (101), illustrated for reference below the said cross-section. The thread (105), carved into the screw head (101) damages the intersection lines (95) of the curved sections (94) in the locking process in the way shown in FIG. 4A. The damage (99) resulting from the thread (105) cutting follows the length of the screw as shown by the line of damage (98). FIG. 4B shows another case where the screw is screwed at an angle of 10° relative to the bore (91) axis. The thread (105), carved into the screw head (101) damages the intersection lines (95) of the curved sections (94) in the locking process as shown in FIG. 4B. The damage (99) resulting from the thread (105) cutting follows the length of the screw as shown by the line of damage (98). By comparing FIGS. 4A and 4B the damages (99) of locking the screw head (101)

with the thread (105) in a position inclined relative to the bore (91) axis is evident. This invention represents an inverse technical solution with respect to the solution disclosed hereby. The screw, according to this invention, contains a number of curved surfaces, while a standard or non-standard thread is carved into the bone plate. The new technical solution according to the present invention will be qualitatively and quantitatively compared with the solution from the invention WO2015/020789A1 of the background art.

The mechanical testing of the inverse technical solutions shows that the new technical solution is at least as good as the solution presented in the document WO2015/020789A1 of the background art, while being simpler to produce.

SUMMARY

The present disclosure discloses a novel screw design with a variable locking angle into the bone plate. According to one or more embodiments, said screw can consist of:
- a screw head with curved surfaces and contact surfaces, as well as a centrally placed star-shaped socket for receiving a fastening tool, located on the upper side of said head; and
- a screw body ending with a tip that enters the bone first; where the said screw body is equipped with a self-cutting thread which extends from the joint between the screw head and the screw body along to the tip of the screw.

The said screw can be characterized by one, some, or all of the following features:
- said screw head is formed from a rotationally symmetric truncated cone of height h, with a base radius Rout on which said star-shaped socket is centrally positioned and where the cone side is inclined at an angle Y relative to the axis of said cone which coincides with the screw axis;
- where n equally curved surfaces, n≥4, are carved into said cone and extend from the upper edge of the screw head to the bottom edge of the said head and where each of the said surfaces forms a portion of the cylindrical surface with the curvature Rc, where the longitudinal axis of said cylindrical surface lies on the straight line II which is parallel to the cone surface and inclined at an angle Y relative to the axis of the screw, and where the intersections of all straight lines II of the said n cylindrical surfaces with the plane perpendicular to the screw axes form vertices of a regular polygon with n sides;
- where the said curved surfaces are interconnected with the identical contact surfaces of the truncated cone, both extending from the upper edge to the bottom edge of the screw head;
- where the upper edge is partly formed from the points of contact surfaces that lie on the radius Rout with the center on the axis of the screw, and from the upper edges of the curved surfaces in a way that the highest point of each said surface lies on the radius Rin in a plane parallel to the plane containing the base of the radius Rout, provided that Rin<Rout; and
- where the bottom edge is formed from the ends of contact surfaces and the curved surfaces so that it enters the joint between the head and the screw body.

The screw head, with curved surfaces and contact surfaces, can be formed without thread on the said surfaces. According to one or more embodiments, preferred values can be selected to be:

a) n=6, 8, 10 or 12;
b) z=Rin/Rout/Rc is selected to be $0.3 \text{ mm}^{-1} < z < 3.0 \text{ mm}^{-1}$; and
c) $5° < Y < 30°$.

According to one or more embodiments of the present disclosure, the preferred angle Y is 9°, which selection can allow the locking process wherein the maximum applicable locking angle is 20° measured with respect to the screw axis in all directions. A locking system of screws into the plate, according one or more embodiments of the present disclosure, can consist of:
- one or more screws whose head hardness is lower than the hardness of the material used to form the bone plate; and
- a bone plate with a geometry adapted for bone fixation, with at least two bores located within said geometry, where each bore has a thread of a conical shape with the slope δ in relation to the bore axis and which is capable of receiving the conically-shaped screw head.

The selected height h can be greater than the thickness of the bone plate. The bore thread slope δ can be greater or equal to the slope Y of the screw head and the corresponding contact and curved surfaces. The insertion of the screw, which can be at a selected angle in the range from −20° to 20° relative to the bore axis, can cause the bore thread to be cut into the contact and curved surfaces of the screw head. Said cutting can cause damage on the screw head surfaces which can keep the said screw locked into the corresponding plate.

According to a preferred embodiment, the height h can be selected to be from 0.5 to 1.6 of the plate thickness and δ can be selected to be from 5° to 30°.

Said technical solution(s) can be applicable for the bone plates where bores have a continuous thread, as well as where each bore has a thread which is not continuous but has threaded segments and segments where the thread is absent. Such a locking system can be useful in veterinary and human medicine, as non-limiting examples.

A BRIEF DESCRIPTION OF THE FIGURES

FIG. 2 depicts a screw that locks into the said plate, while

DETAILED DESCRIPTION

Embodiments of the disclosed subject matter can relate to a screw (10) with a variable angle of locking into a bone plate (30), where the head (20) of the said screw is locked into a bore (31) of the plate (30). Embodiments of the disclosed subject matter can also involve a corresponding locking system of screw (10)-plate (30) as illustrated in FIG. 5C. The plate (30) may be formed of an arbitrary geometry, but for simplicity reasons the plate (30) is illustrated in FIG. 5C with a series of evenly spaced bores (31). The spacing of each bore (31) should be such to allow optimum plate (30) fixation to the desired bone. According to embodiments of the present disclosure, each of the bores (31) is made with a continuously machined thread (32), with a slope, for instance, as shown in FIG. 5B. FIG. 5B shows one continuous thread (32), carved conically at an angle δ relative to the bore (31) axis where the side of the cone accompanying the thread (32) is marked with straight line Δ. According to one or more embodiments, it may be desirable that the angle δ is greater than or equal to angle Y, which can define the cone of the screw head (20) which is suitably locked by the corresponding thread (32) when the value is about 2 Y. In practice, the value δ can be chosen in the range from 5° to 30° as shown in FIGS. 5A and 5B.

Embodiments of the present disclosure, however, are not limited to tapered threads (32) illustrated in FIG. 5B, but can also include cylindrical threads of a constant cross-section (δ=0). However, a due care may need to be undertaken when choosing dimensions of a corresponding screw (10) whose head (20) is locked by said thread (32). In addition to the already mentioned continuous conical and cylindrical geometry, the thread (32) can be machined in a way which is not continuous but has segments which are threaded and segments where the thread is absent, i.e., with the thread made only on segments of the bore (31). If there is a need for such a technical solution, it is also possible to imagine a plate (30) which combines bores (31) with several different types of previously mentioned threads (32). For machining simplicity and for obtaining optimum locking performances, for instance, the processing of all bores (31) of the bone plate (30) can be performed in such a way that all threads (32) are selected to be of conical type where δ≈2 Y, which can significantly reduce the production costs of such plates (30). According to one or more embodiments of the present disclosure, the plate (30) can be made of a material exhibiting hardness higher than the hardness of the screw head (20), preferably of titanium used for medicinal purposes, e.g., grade 5, and for the corresponding screw (10) or screw head (20) of titanium grade 2. FIG. 5C illustrates such a screw (10) before insertion into the plate (30).

Figure 7A:
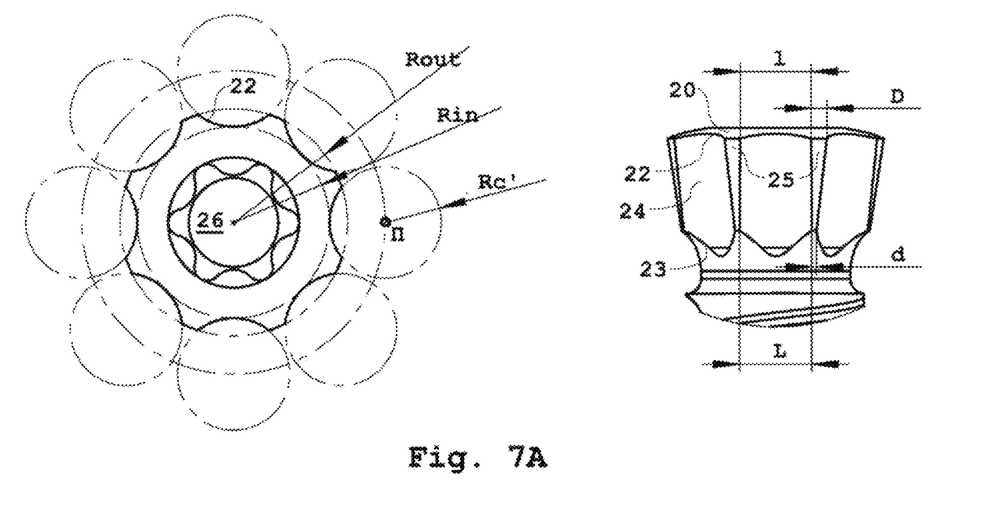
FIGS. 7A, 7B, 7C, 7D, 7E and 7F depict a screw head design according to one or more embodiments of the present disclosure in the case when n is selected to be equal to 8, 10 and 12 curved surfaces on the screw head, for a screw of the same head radius Rout with variations in the size of the curved surfaces.
Figure 7B:
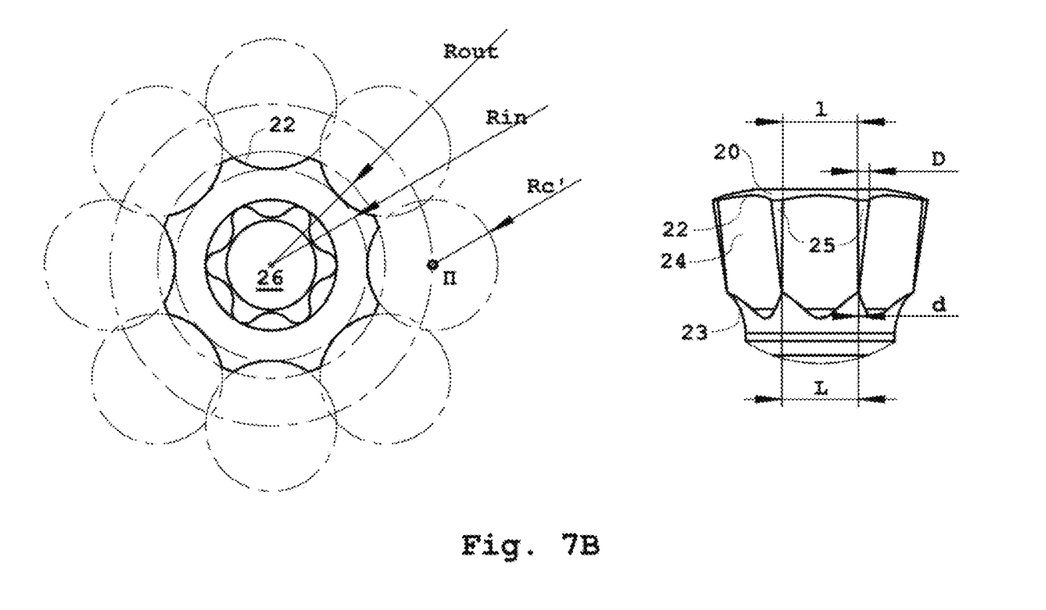

In one or more embodiments of the present disclosure, the screw (10) can consist of a screw head (20) with machined curved surfaces (24) and contact surfaces (25), as well as a centrally placed socket shaped like a star (26) for receiving the fastening tool into, located on the upper side of said head, as shown in FIG. 7A. The star-shaped socket (26) can be of an arbitrary geometry suitable for receiving a fastening tool tip and made in a way which prevents the tools from popping out of this socket, e.g., a Phillips or an Allen type tool which enables accurate handling by the operator. The screw body (13) ends with a tip (12) of the screw (10) that enters the bone first. The screw body (13) is equipped with a self-cutting thread (14) which extends from the joint (16) between the screw head (20) and the screw body (13) to the said screw tip (12).

Figure 5A:
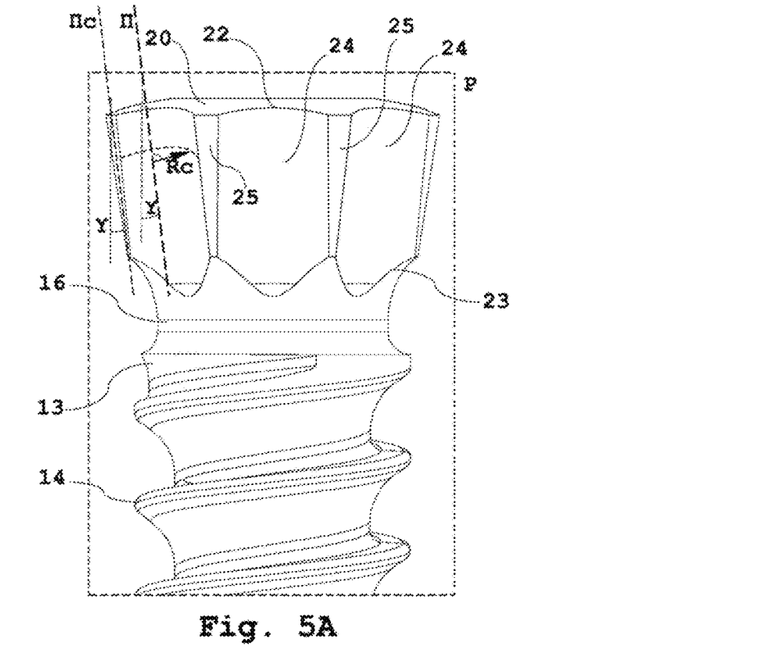
FIG. 5A represents detail P from FIG. 5C and depicts the newly designed screw head that can be locked into the bore made in the bone plate shown in FIG. 5B.
Figures 5B, 5C:
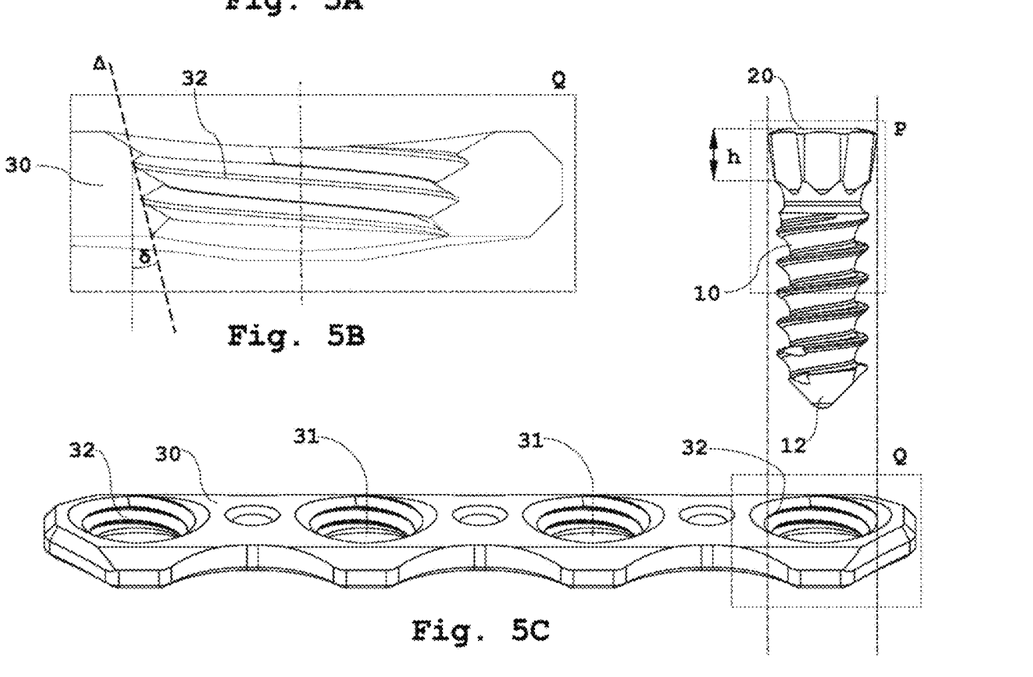
FIG. 5B is a cross-section of the bone plate detail, marked with Q, in FIG. 5C.

However, the head (20) of the screw (10), illustrated in FIG. 5A as a detail in FIG. 5C, can represents another patentable distinction of one or more embodiments of the disclosed subject matter. As mentioned before, fewer screws (10) are often used in surgical interventions than there are bores (31) with threads (32) made on bone plates (30). Bearing this in mind, a locking system that has more bores (31) created in a simpler and more economical way on plates (30), while the more demanding machining may be required for the screws (10) only—has obvious advantages in the art, rendering the locking system cheaper.

Figure 7C:
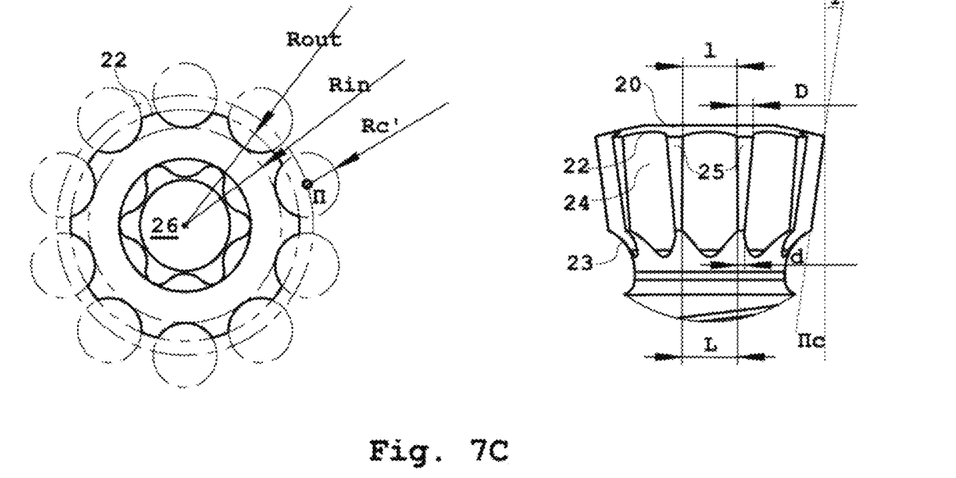
Figure 7D:
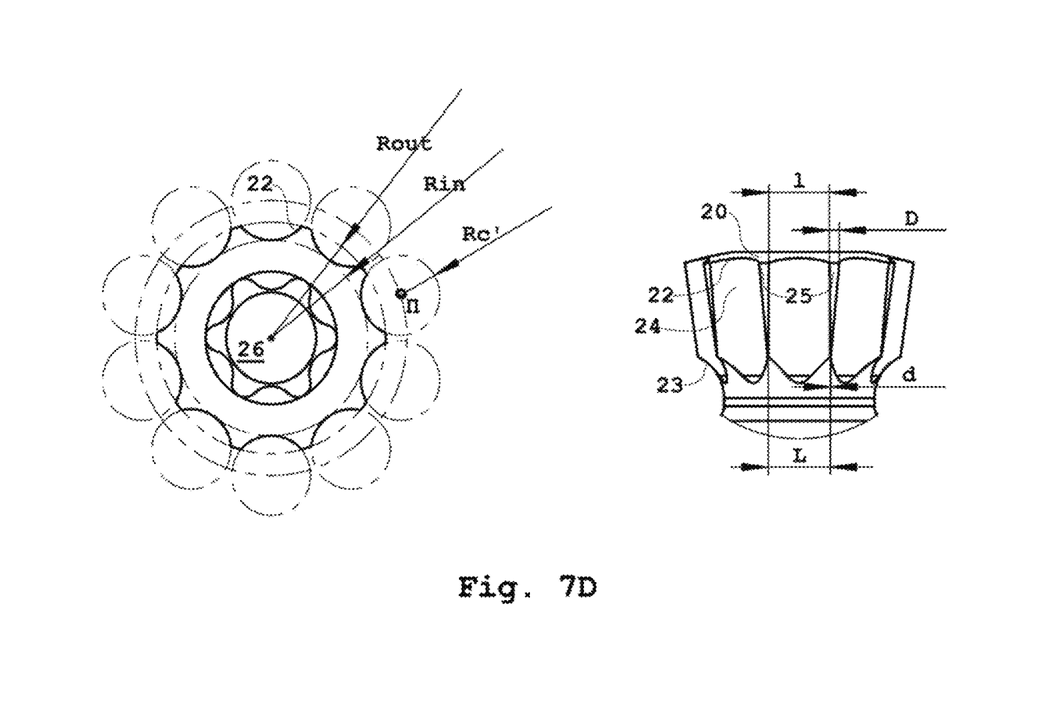
Figure 7E:
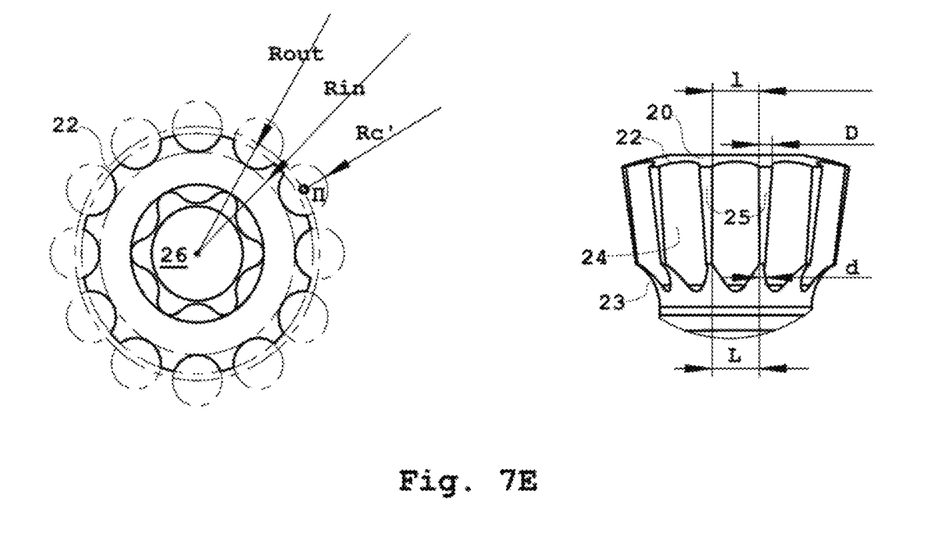
Figure 7F:
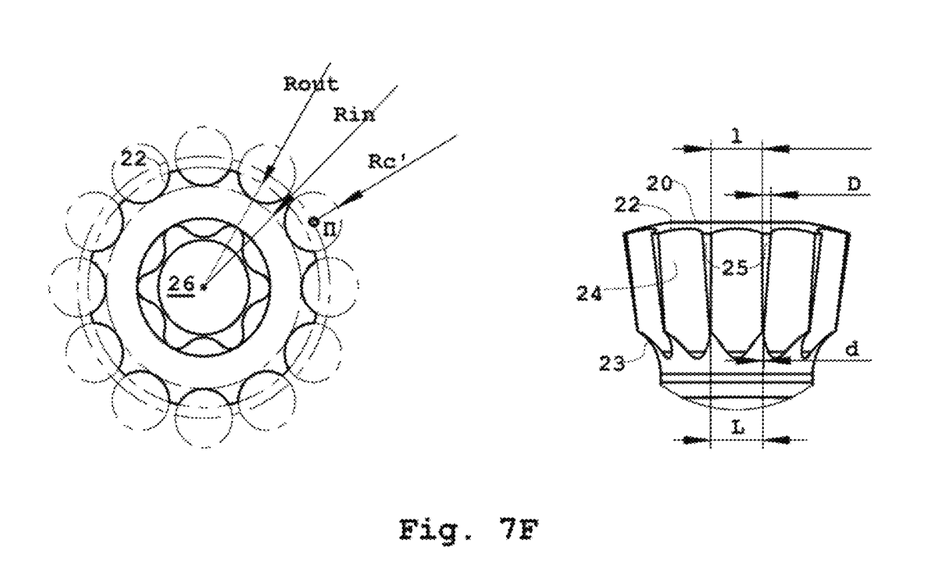

The screw head (20), according to one or more embodiments of the disclosed subject matter, can be formed from a rotationally symmetric truncated cone of height h, see FIGS. 5C and 5A as well as FIGS. 7A-7F. This truncated cone is directed with its missing tip towards the tip (12) of the screw (10). The base of this rotating cone is designed with radius Rout, see FIGS. 7A-7F, and is projecting slightly outwards in a way that the star-shaped socket (26) is situated within the said cone. The side of the cone is inclined at the angle Y in relation to the longitudinal axis of the said cone, as indicated in FIGS. 7C and 5A. The straight line πc is a line that lies on the side of the cone in at least two different points and cuts the cone rotational axis in just one point. Consequently, each such straight line πc is inclined at Y angle in relation to the longitudinal axis of the said cone, see, for example, FIG. 5A.

In order to obtain a screw head shape according to one or more embodiments of the present disclosure, the manufacturing process may be considered. Screws (10) are most often produced using CNC (Computer Numerical Control) technology and it is therefore may be useful to use tool trajectories that are compatible with the production technology. The screw head (20) according one or more embodiments of the present disclosure, when viewed from the upper perspective, see FIGS. 7A-7F, is a part with side grooves, i.e., curved surfaces which have been machined out. According to one or more embodiments of the present disclosure, the head (20) is formed by milling curved surfaces (24) of the truncated cone as shown in FIG. 5A. Each of the curved surfaces (24) is formed as a portion of the cylindrically shaped surface, where the cylinder itself has a radius Rc and where the axis of that cylinder lies on straight line H. The straight line II is inclined at an angle Y relative to the longitudinal axis of the cone into which curved surfaces (24) are carved as shown in FIG. 5A. According to one or more embodiments of the present disclosure, n equally curved surfaces (24) are carved into said cone, as illustrated in FIGS. 7A-7F. The bundle of straight lines π which are inclined at an angle Y forms vertices of a regular polygon with n sides, when these lines intersect the plane perpendicular to the longitudinal axis of the cone. According to one or more embodiments, it may be desirable that n is equal or greater than 4, for instance, when n=8, 10 or 12. When curved surfaces (24) are carved, then the truncated cone surfaces that remain between them are portions of the side of the truncated cone that connect them and represent the contact surfaces (25). In this way, alternately shaped curved surfaces (24) and the contact surfaces (25) are extended from the upper edge (22) to the bottom edge (23) of the head (20), where said head (20) passes into the joint (16) between the head (20) and the screw body (13).

FIGS. 7A-7F show projections of the characteristic radii Rout, Rin, and Rc' into the plane perpendicular to the longitudinal axis of the cone and the corresponding design of the screw head (20) with such a geometry disclosed in Table 1. The size of Rout represents the radius of the cone base, Rin is the smallest distance from the upper edge (22), i.e., the highest point of the curved surface (24) on the screw head (20) to the screw (10) axis. Value Rc' represents a projection cylindrical curvature Rc of the surfaces (24) into the plane perpendicular to the cone axis. L represents the largest distance between two contact surfaces (25) located closer to the bottom edge (23) where the cylinder with radius Rc plunges deeper into the cone, and l represents the smallest distance between the contact surfaces (25) located closer to the upper edge (22) of the head (20). D represents the maximum distance between two adjacent curved surfaces (24), and d is the smallest distance, close to the bottom edge (23). Value A represents the area of contact surface (25) of the screw designed in this way. A side-by-side comparison of the screw head (20) performances was made for the constant values of Rout and Rin; only parameter Rc was varied by approx. 15% and the number of curved surfaces (24) is selected to be 8, 10 and 12. The parameters of such variations for 2.4 mm screw are shown in Table 1 below:

TABLE 1

| n (FIG.) | Rout [mm] | Rin [mm] | Rc [mm] | l [mm] | L [mm] | D [mm] | d [mm] | A [mm$^2$] |
|---|---|---|---|---|---|---|---|---|
| 8 (7A) | 1.524 | 1.285 | 0.750 | 0.952 | 0.970 | 0.229 | 0.068 | 0.184 |
| 8 (7B) | 1.524 | 1.285 | 0.875 | 1.010 | 1.028 | 0.167 | 0.006 | 0.107 |
| 10 (7C) | 1.524 | 1.285 | 0.425 | 0.724 | 0.740 | 0.226 | 0.098 | 0.202 |
| 10 (7D) | 1.524 | 1.285 | 0.525 | 0.811 | 0.829 | 0.137 | 0.006 | 0.089 |
| 12 (7E) | 1.524 | 1.285 | 0.325 | 0.612 | 0.622 | 0.182 | 0.079 | 0.162 |
| 12 (7F) | 1.524 | 1.285 | 0.375 | 0.672 | 0.686 | 0.120 | 0.013 | 0.083 |

Figure 6A:
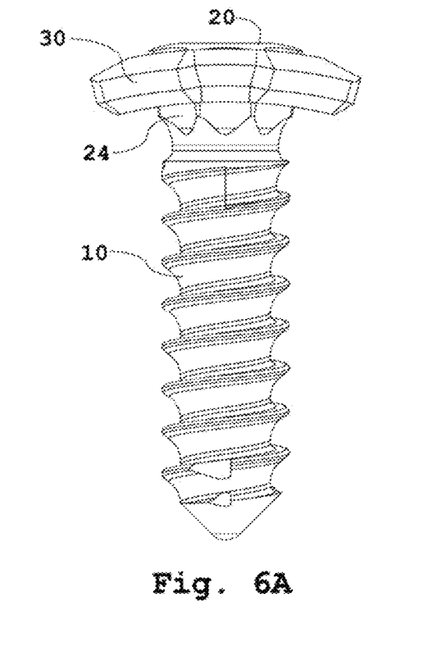
FIG. 6A illustrates a position of the locked screw in the case when the screw head is fixed at an angle of 0° in relation to the bore axis.
Figure 6B:
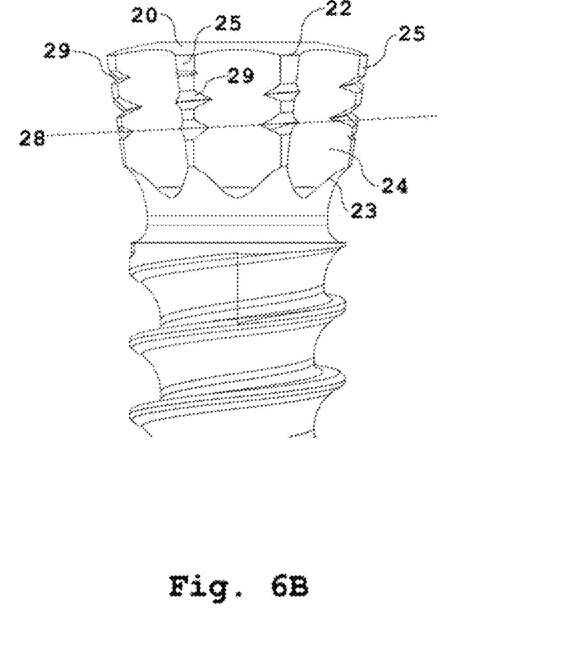
FIG. 6B shows exemplary damage that may result to the screw head according to one or more embodiments of the present disclosure.
Figure 6C:
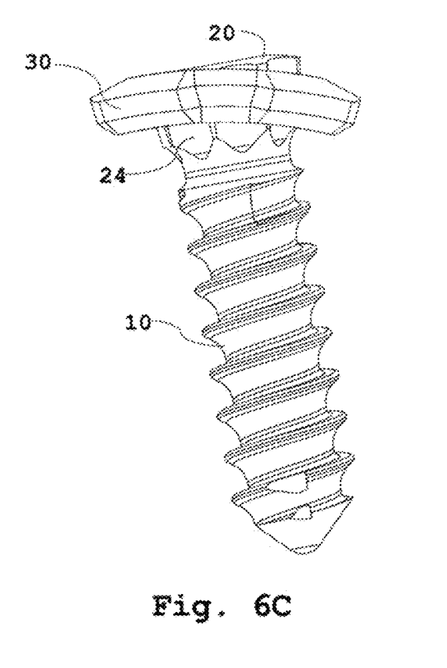
FIG. 6C illustrates a position of the locked screw in the case when the screw head is fixed at an angle of 10° in relation to the bore axis.
Figure 6D:
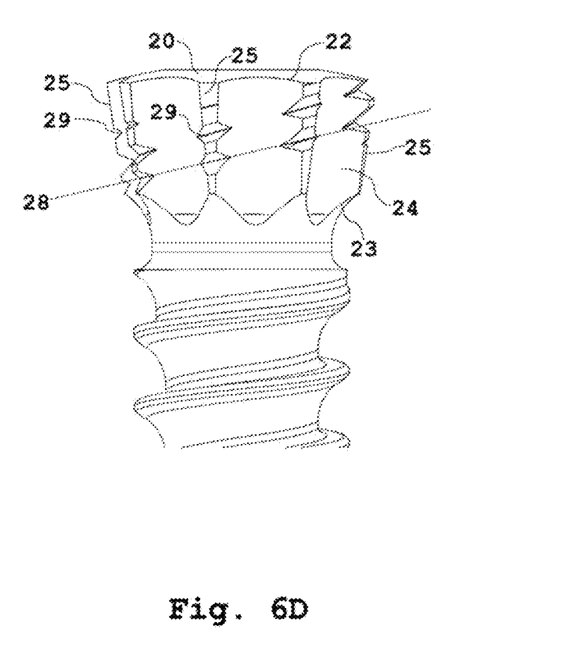
FIG. 6D shows exemplary damage that may result to the screw head according to one or more embodiments of the present disclosure.

When designing the screw, according to embodiments of the disclosed subject matter particular care of the surface A layout may be taken, specifically of the contact surface (25) area once the machining of the cone head (20) is finished, where said contact surfaces (25) have a key function in the locking process. The locking process is shown in a series of FIGS. 6A-6D. FIG. 6A is a side view of the plate (30) into which the screw (10) is locked at an angle of 0°. FIG. 6B shows damage (29) that occurs on the contact surfaces (25) and the curved surfaces (24) of said screw head (20). The line of damage (28) ascent coincides with the thread (32) created in the bore (31). In the same way FIG. 6C represents a side view of the plate (30) into which the screw (10) is locked at an angle of 10°. FIG. 6D illustrates damage (29) that occurs on the contact surfaces (25) and the curved surfaces (24) of said screw head (20) during locking at an angle of 10°. The damage occurs on the screw head (20) made of a material that is softer than the material of the plate (30).

In practice, two extremes can be avoided, i.e., a too large contact surface (25) which can prevent easy occurrence of damage (29), but locks the head (20) into the plate perfectly, and a very small contact surface (25) that locks the head (20) into the plate (30) less than perfectly, but handling such a screw is relatively simple.

In modelling the screw (10) layouts and cutting-in forces that cause damages (29) the following values were found as optimal for the given screw head design according to one or more embodiments of the disclosed subject matter.

Table 2 shows the values for screws of 2.4 mm, 3.5 mm and 5.0 mm that are used in practice, with 8, 10 or 12 curved surfaces (24) and acceptable parameters D and d, defining the largest and the smallest spacing between the curved surfaces (24) and thus the amount of the contact surface (25) that participates in the locking process. It should be emphasized that the sizes D and d are directly related to the chosen range of the radius of curvature Rc and the values Rin and Rout.

TABLE 2

| Screw [mm] | n | Rout [mm] | Rin [mm] | Rc [mm] | D [mm] | d [mm] |
|---|---|---|---|---|---|---|
| 2.4 | 8 | 1.524 | 1.285 | 0.750-0.875 | 0.229-0.167 | 0.068-0.006 |
| 2.4 | 10 | 1.524 | 1.285 | 0.425-0.525 | 0.226-0.137 | 0.098-0.006 |
| 2.4 | 12 | 1.524 | 1.285 | 0.325-0.375 | 0.182-0.120 | 0.079-0.013 |
| 3.5 | 8 | 2.477 | 2.100 | 1.400-1.550 | 0.304-0.241 | 0.074-0.010 |
| 3.5 | 10 | 2.477 | 2.100 | 0.800-0.910 | 0.281-0.196 | 0.095-0.007 |
| 3.5 | 12 | 2.477 | 2.100 | 0.550-0.650 | 0.276-0.162 | 0.127-0.007 |
| 5.0 | 8 | 3.200 | 2.800 | 2.125-2.300 | 0.463-0.408 | 0.062-0.007 |
| 5.0 | 10 | 3.200 | 2.800 | 1.150-1.275 | 0.409-0.332 | 0.081-0.001 |
| 5.0 | 12 | 3.200 | 2.800 | 0.800-0.850 | 0.347-0.302 | 0.077-0.028 |

A comparison between embodiments of the present disclosure and the locking system disclosed by the document WO2015/020789A1 is given below. The analysis was carried out by performing the cyclic testing of the locking features by bending the screw of 2.4 mm in diameter locked into a 1 mm thick plate with 4 bores by parallelly examining the solution presented in WO2015/020789A1 and embodiments of the present disclosure in a fatigue test (LFV 50-HH, Walter+Bai AG, Switzerland, production year 2006). The selected angles of locking the screws into the plates were 0°, 10°, 15° and 20° in relation to the bore (31) or bore (91) axis, as shown in Table 3, which contains the test parameters:

TABLE 3

| Screw angle [°] | Fsr [N] | Fa [N] | f [Hz] | N [—] | Fd [kN] | F [N] |
|---|---|---|---|---|---|---|
| 0 | 38 | 32 | 1, 4 | 5000 | 6, 3 | 6-70 |
| 10 | 33 | 27 | 1, 4 | 5000 | 6, 3 | 6-60 |
| 15 | 27 | 23 | 1, 4 | 5000 | 6, 3 | 4-50 |
| 20 | 22 | 18 | 1, 4 | 5000 | 6, 3 | 4-40 | where the following abbreviations are used:

Fsr—mean force,

Fa—force amplitude

F—force range Fsr+/−Fa, f—frequency of cyclic loading,

N—number of load cycles, and

Fd—nominal force of the force transducer.

The results of the bending test, using 3 different samples in each experiment, with the screw locked into the plate under cyclic load are shown in the tables below, where the following notation is used:

Smax—maximum screw displacement,

Smin—minimal screw displacement,

Δs=Smax—Smin,

Fmax—maximum force at Smax,

Stiffness—Fmax/Smax ratio.

The comparison of the technical solution presented in FIGS. 1-4B and the new locking system according to one or more embodiments of the disclosed subject matter is elaborated side-by-side in the tables below:

TABLE 4A background art

| Screw angle 0° | Smax [mm] | Smin [mm] | ΔS [mm] | Fmax [N] | Stiffness [N/mm] |
|---|---|---|---|---|---|
| Sample 1 | 0.249 | 0.067 | 0.183 | 69.30 | 277.87 |
| Sample 2 | 0.364 | 0.155 | 0.209 | 70.80 | 194.43 |
| Sample 3 | 0.279 | 0.106 | 0.173 | 68.70 | 246.41 |
| Mean value | 0.297 | 0.109 | 0.188 | 69.60 | 239.57 |
| Std. dev. | 0.060 | 0.044 | 0.018 | 1.082 | 42.140 |

TABLE 4B

Present embodiment(s)

| Screw angle 0° | Smax [mm] | Smin [mm] | ΔS [mm] | Fmax [N] | Stiffness [N/mm] |
|---|---|---|---|---|---|
| Sample 1 | 0.267 | 0.072 | 0.195 | 67.80 | 253.89 |
| Sample 2 | 0.262 | 0.071 | 0.191 | 71.30 | 271.83 |
| Sample 3 | 0.343 | 0.137 | 0.206 | 71.30 | 207.96 |
| Mean value | 0.291 | 0.093 | 0.198 | 70.13 | 244.56 |
| Std. dev. | 0.045 | 0.038 | 0.008 | 2.021 | 32.938 |

At the very least, for the locking angle of 0° the system according to one or more embodiments of the present disclosure can be significantly simpler to produce.

TABLE 5A background art

| Screw angle 10° | Smax [mm] | Smin [mm] | ΔS [mm] | Fmax [N] | Stiffness [N/mm] |
|---|---|---|---|---|---|
| Sample 1 | 0.213 | 0.064 | 0.149 | 60.70 | 285.04 |
| Sample 2 | 0.292 | 0.115 | 0.177 | 60.80 | 208.47 |
| Sample 3 | 0.419 | 0.217 | 0.202 | 59.70 | 142.38 |
| Mean value | 0.308 | 0.132 | 0.176 | 60.40 | 211.96 |
| Std. dev. | 0.104 | 0.078 | 0.027 | 0.608 | 71.396 |

TABLE 5B

Present embodiment(s)

| Screw angle 10° | Smax [mm] | Smin [mm] | ΔS [mm] | Fmax [N] | Stiffness [N/mm] |
|---|---|---|---|---|---|
| Sample 1 | 0.270 | 0.092 | 0.178 | 58.80 | 217.82 |
| Sample 2 | 0.302 | 0.101 | 0.200 | 60.90 | 201.92 |
| Sample 3 | 0.254 | 0.078 | 0.175 | 59.00 | 232.47 |
| Mean value | 0.275 | 0.090 | 0.185 | 59.57 | 217.40 |
| Std. dev. | 0.024 | 0.011 | 0.014 | 1.159 | 15.276 |

The results show that the mean value of the maximum screw displacement can be lower in embodiments of the present disclosure, and that stiffness, when the maximum force is taken into consideration for both technical solutions, may exhibit similar values for a locking angle of 10°.

TABLE 6A background art

| Screw angle 15° | Smax [mm] | Smin [mm] | ΔS [mm] | Fmax [N] | Stiffness [N/mm] |
|---|---|---|---|---|---|
| Sample 1 | 0.257 | 0.114 | 0.143 | 45.70 | 177.51 |
| Sample 2 | 0.209 | 0.046 | 0.163 | 49.60 | 236.98 |
| Sample 3 | 0.250 | 0.081 | 0.168 | 49.10 | 196.60 |
| Mean value | 0.239 | 0.081 | 0.158 | 48.13 | 203.696 |
| Std. dev. | 0.026 | 0.034 | 0.013 | 2.122 | 30.364 |

TABLE 6B

Present embodiment(s)

| Screw angle 15° | Smax [mm] | Smin [mm] | ΔS [mm] | Fmax [N] | Stiffness [N/mm] |
|---|---|---|---|---|---|
| Sample 1 | 0.220 | 0.047 | 0.172 | 49.60 | 225.81 |
| Sample 2 | 0.258 | 0.080 | 0.178 | 51.40 | 199.03 |
| Sample 3 | 0.238 | 0.068 | 0.170 | 49.80 | 209.60 |
| Mean value | 0.239 | 0.065 | 0.173 | 50.27 | 211.48 |
| Std. dev. | 0.019 | 0.017 | 0.004 | 0.99 | 13.49 |

The results show once again that the mean value of the maximum screw displacement can be the same, and that stiffness may be similar in both technical solutions, taking the maximum force of a similar amount into account for a locking angle of 15°.

TABLE 7A background art

| Screw angle 20° | Smax [mm] | Smin [mm] | ΔS [mm] | Fmax [N] | Stiffness [N/mm] |
|---|---|---|---|---|---|
| Sample 1 | 0.259 | 0.135 | 0.124 | 39.30 | 151.77 |
| Sample 2 | 0.188 | 0.057 | 0.131 | 39.00 | 207.50 |
| Sample 3 | 0.168 | 0.042 | 0.125 | 39.60 | 236.07 |
| Mean value | 0.205 | 0.078 | 0.127 | 39.30 | 198.445 |
| Std. dev. | 0.048 | 0.050 | 0.004 | 0.300 | 42.873 |

TABLE 7B

Present embodiment(s)

| Screw angle 20° | Smax [mm] | Smin [mm] | ΔS [mm] | Fmax [N] | Stiffness [N/mm] |
|---|---|---|---|---|---|
| Sample 1 | 0.164 | 0.024 | 0.141 | 39.40 | 239.59 |
| Sample 2 | 0.156 | 0.026 | 0.130 | 39.00 | 249.52 |
| Sample 3 | 0.171 | 0.018 | 0.153 | 39.40 | 230.34 |
| Mean value | 0.164 | 0.023 | 0.141 | 39.27 | 239.82 |
| Std. dev. | 0.007 | 0.004 | 0.011 | 0.23 | 9.59 |

The obtained results show a comparison among background art and one or more embodiments of the present disclosure. The stiffness according to one or more embodiments of the present disclosure can be higher for a locking angle of 20° than in the case of background art.

From the results shown in Tables 4, 5, 6 and 7 it is possible to conclude that, within the experimental error, the locking system of one or more embodiments of the present disclosure can be, for instance, even better (stiffer) as the inclination of the screw head (20) increases in relation to the bore (31) axis, which is certainly an unexpected result for an average person skilled in the art. This unexpected result, therefore, indicates an inventive step in the presented new technical solution. It is necessary to emphasize once again that the proposed new locking system according to embodiments of the disclosed subject matter can transfer all the machining complexity or processing from the plate (30) to the screw (10), more specifically, to the screw head (20).

REFERENCES

References of the New Technical Solution
(Representative of Examples Only)

10 screw for the plate 30
12 tip of the screw 10
13 screw body with a self-cutting thread 14
14 self-cutting thread
16 joint between screw head 20 and screw body 13
20 screw head
22 upper edge of the screw head 20
23 bottom edge of the screw head 20
24 curved surface formed in the screw head 20
25 contact surface between the curved surfaces 24
26 star-shaped socket for receiving a fastening tool
28 line of ascent of damage 29
29 damage caused by carving thread 32 into the contact surfaces 25 and curved surfaces 24
30 plate
31 bore for locking the screw head 20
32 thread in the bore 31
Rin the smallest radius of the upper edge 22 of the screw head 20
Rout the largest radius of the upper edge 22 of the screw head 20
Rc curvature radius of the machined surface 24 measured perpendicular to the direction of the tool movement along the straight line $\pi$
Rc' projection of Rc on the plane perpendicular to the screw 10 axis
L distance between two adjacent contact surfaces 25 along the edge 23
l distance between two adjacent contact surfaces 25 along the edge 22
D contact surface 25 width along the edge 22
d contact surface 25 width along the edge 23
h screw head height
$\pi$ straight line parallel to the cone sides of the screw head 20
$\pi$c straight line situated on the contact surface 25
Y inclination angle of the straight line II in relation to the screw 10 axis
$\Delta$ the slope line of the thread 32 in the bore 31
$\delta$ angle of the slope line $\Delta$ in relation to the bore 31 axis
n number of curved surfaces 24 on the head 20 of the screw 10
P, Q details References of the Background Art 90 plate
91 bore for receiving the screw head 101
92 upper edge of the bore 91
93 bottom edge of the bore 91
94 curved section of the bore 91
95 line of intersection of sections 94
96 contact area at the intersection of sections 94
98 line of ascent of damage 99
99 damage caused by screw head threading 105
100 screw for the plate 90
101 screw head with the thread 105
102 tip of the screw 100
103 body of the screw 100 with the self-cutting thread 104
104 self-cutting thread
105 thread of the screw head 101
106 joint between the screw head 101 and the screw body 103
$\delta'$ inclination angle of curved sections 94 which is cone-shaped, in relation to the bore 91 axis
S detail

The invention claimed is:

1. A screw with a variable locking angle into a bone plate, the screw comprising:
   a screw head with carved surfaces and contact surfaces, as well as a centrally placed star-shaped socket to receive a fastening tool, located on an upper side of said screw head; and
   a screw body ending with a tip portion to enter a bone first, where said screw body is equipped with a self-cutting thread which extends from a joint between the screw head and the screw body to the tip portion of the screw,
   wherein said screw head is formed from a rotationally symmetric truncated cone of height h, with a base radius Rout on which said star-shaped socket is centrally positioned and where a cone side is inclined at an angle Y relative to an axis of said rotationally symmetric truncated cone which coincides with a screw axis of the screw,
   wherein n of the carved surfaces, where n≥4, are carved into said rotationally symmetric truncated cone and extend from an upper edge of the screw head to a bottom edge of said screw head,
   wherein said carved surfaces are interconnected with the contact surfaces of the rotationally symmetric truncated cone, both extending from the upper edge to the bottom edge of the screw head,
   wherein the upper edge is partly formed from points of the contact surfaces that lie on the base radius Rout, and from upper edges of the carved surfaces in a way that a highest point of each said carved surface lies on a radius Rin in a plane parallel to a plane containing the base radius Rout, provided that Rin<Rout,
   wherein the bottom edge is formed from ends of contact surfaces and the carved surfaces and leads to the joint between the screw head and the screw body,
   wherein the screw head, with the carved surfaces and the contact surfaces, is formed without any thread on the carved surfaces and the contact surfaces, and
   wherein the contact surfaces and the carved surfaces are adapted to be cut into and damaged by a thread of a bore when the screw is inserted into the bore.

2. The screw according to claim 1, wherein the number of carved surfaces n distributed around the perimeter of the screw head is selected to be n=6, 8, 10, or 12, wherein the value Y is selected to be 5°<Y<30°.

3. The screw according to claim 2, wherein the angle Y is 9°.

4. The screw according to claim 1, wherein a maximum applicable locking angle for the screw is 20° measured with respect to the screw axis in all directions.

5. The screw according to claim 1, wherein each of the contact surfaces is flat and linear along an entire length and an entire width of the contact surface.

6. A locking system consisting of:
   one or more screws whose screw head, which is conically-shaped, has a hardness that is lower than a hardness of a material used to form a bone plate; and the bone plate with a geometry adapted for bone fixation, with at least two bores located within said geometry, where each said bore has a thread of a conical shape with a slope $\delta$ in relation to a bore axis of the bore and which is configured to receive the screw head of the screw, wherein each of the one or more screws includes:

the screw head, with carved surfaces and contact surfaces, as well as a centrally placed star-shaped socket to receive a fastening tool, located on an upper side of said screw head, and a screw body ending with a tip portion to enter the bone first, where said screw body is equipped with a self-cutting thread which extends from a joint between the screw head and the screw body to the tip portion of the screw, wherein said screw head is formed from a rotationally symmetric truncated cone of height h, with a base radius Rout on which said star-shaped socket is centrally positioned and where a cone side is inclined at an angle Y relative to an axis of said rotationally symmetric truncated cone which coincides with a screw axis of the screw, wherein n of the carved surfaces, where n≥4, are carved into said rotationally symmetric truncated cone and extend from an upper edge of the screw head to a bottom edge of said screw head, wherein said carved surfaces are interconnected with the contact surfaces of the rotationally symmetric truncated cone, both extending from the upper edge to the bottom edge of the screw head, wherein the upper edge is partly formed from points of the contact surfaces that lie on the base radius Rout, and from upper edges of the carved surfaces in a way that a highest point of each said carved surface lies on a radius Rin in a plane parallel to a plane containing the base radius Rout, provided that Rin<Rout, wherein the bottom edge is formed from ends of contact surfaces and the carved surfaces and leads to the joint between the screw head and the screw body, wherein the screw head, with the carved surfaces and the contact surfaces, is formed without any thread on the carved surfaces and the contact surfaces, wherein an inner bore slope $\delta$ is greater than or equal to the angle Y of the screw head with the corresponding contact surfaces and carved surfaces, and wherein the system is adapted to implement a locking process whereby insertion of the screw, at a selected angle in a range from −20° to 20° relatively to the bore axis, causes the thread of the bore to be cut into the contact surfaces and carved surfaces of the screw head causing damages on the contact surfaces and the carved surfaces that keep the screw locked into the bone plate.

7. The locking system according to claim 6, wherein the height h is selected to be from 0.5 to 1.6 of the thickness of the bone plate and the inner bore slope $\delta$ is selected to be from 5° to 30°.

8. The locking system according to claim 6, wherein the thread of each said bore is continuous.

9. The locking system according to claim 6, wherein the thread of each said bore is not continuous but has segments with a thread and segments where the thread is absent.

10. The locking system according to claim 6, wherein a minimum thickness of the bone plate is 1 mm or less.

11. The locking system according to claim 6, wherein the number of carved surfaces n distributed around the perimeter of the screw head is selected to be n=6, 8, 10, or 12, wherein the value Y is selected to be 5°<Y<30°.

12. The locking system according to claim 11, wherein the angle Y is 9°.

13. The locking system according to claim 6, wherein a maximum applicable locking angle for the screw is 20° measured with respect to the screw axis in all directions.

\* \* \* \* \*